(12) United States Patent
Warden et al.

(10) Patent No.: US 9,446,407 B2
(45) Date of Patent: Sep. 20, 2016

(54) LID MECHANISM

(71) Applicant: Synthetic Genomics, Inc., La Jolla, CA (US)

(72) Inventors: Laurence Warden, Poway, CA (US); Scott Wayne Beaver, San Marcos, CA (US); Mark Henry Becker, Vista, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 0 days.

(21) Appl. No.: 14/800,113

(22) Filed: Jul. 15, 2015

(65) Prior Publication Data

US 2016/0016163 A1 Jan. 21, 2016

Related U.S. Application Data

(60) Provisional application No. 62/025,285, filed on Jul. 16, 2014.

(51) Int. Cl.
| | |
|---|---|
| *B65D 43/26* | (2006.01) |
| *B01L 3/00* | (2006.01) |
| *B01L 7/00* | (2006.01) |
| *B65D 43/14* | (2006.01) |
| *B60K 15/04* | (2006.01) |
| *B65D 43/18* | (2006.01) |

(52) U.S. Cl.
CPC ............... *B01L 3/508* (2013.01); *B01L 3/527* (2013.01); *B01L 7/52* (2013.01); *B65D 43/26* (2013.01); *B01L 3/50853* (2013.01); *B01L 2300/041* (2013.01); *B60K 2015/0425* (2013.01); *B65D 43/14* (2013.01); *B65D 43/18* (2013.01)

(58) Field of Classification Search
CPC .... B65D 43/18; B65D 43/26; B01L 3/50853
See application file for complete search history.

(56) References Cited

U.S. PATENT DOCUMENTS

| | | | |
|---|---|---|---|
| 6,197,572 | B1 | 3/2001 | Schneebeli |
| 6,556,940 | B1 | 4/2003 | Tretiakov et al. |
| 2005/0039818 | A1 | 2/2005 | Bauer |
| 2005/0282270 | A1 | 12/2005 | Shin et al. |
| 2007/0098597 | A1 | 5/2007 | Brunner |

FOREIGN PATENT DOCUMENTS

| | | |
|---|---|---|
| WO | WO 01/46688 A1 | 6/2001 |
| WO | WO 2014/040182 A1 | 3/2014 |

OTHER PUBLICATIONS

International Search Report issued on Oct. 7, 2015, regarding PCT/US2015/040584.

*Primary Examiner* — P. Kathryn Wright
(74) *Attorney, Agent, or Firm* — DLA Piper LLP (US)

(57) ABSTRACT

The invention provides a lid mechanism suitable for use with automated instrumentation. The lid mechanism has a compact design enabling it to function in very small spaces, and therefore on very compact instrumentation. One embodiment of the lid mechanism has a nut positioned around a jackscrew; a motor translationally attached to the nut for driving rotational motion of the nut around the jackscrew and vertical motion of the jackscrew; a main shaft positioned around the jackscrew with a bearing support positioned on the main shaft; a moving support comprising a bearing guide track and positioned on the main shaft so that the bearing support is positioned within the bearing guide track; and a lid plate positioned on the moving support so that vertical movement of the moving support causes vertical movement of the lid plate and rotational movement of the moving support causes rotational movement of the lid plate. Also provided is an automated laboratory instrument having a lid mechanism of the invention.

14 Claims, 5 Drawing Sheets

LID MECHANISM

CROSS-REFERENCE TO RELATED APPLICATIONS

This application claims benefit of priority under 35 U.S.C. §119(e) of U.S. Ser. No. 62/025,285, filed Jul. 16, 2014, the entire contents of which is incorporated herein by reference in its entirety

BACKGROUND

The modern laboratory contains a variety of instrumentation for the analysis and processing of laboratory samples. The area of DNA technology often involves the use of several such instruments, a thermal cycler for the amplification of DNA or a sample heating or cooling chamber being only a few examples. Increasingly these devices are being incorporated as components in high-throughput machines, which are often operated unattended and in a completely automated fashion.

Laboratory instruments such as thermal cyclers or heating or cooling chambers have a manually operated lid that is closed down securely over a DNA sample container to prevent evaporation of samples. While these manually operated lids function well in applications where there is an operator present, they are not compatible with automated devices and do not meet the specific demand requirements of automated devices.

There are currently commercially available these types of instruments that have an automated lid. The automated lid has a simple hinge that is operated by a small motor and rotates about the hinge on the back edge. The motor is commanded to operate by software and the instrument is large enough to accommodate the space necessary for a hinged lid.

There remains a need in the art for a sample container lid that can meet the specific requirements of automated instrumentation. The lid should be able to be operated in an automated fashion and suitable for the limited space requirements of instruments of compact design. These space requirements stem from the instruments often having very limited space in the vertical direction and thus not accommodating a hinged lid.

SUMMARY OF THE INVENTION

The present invention provides a lid mechanism suitable for use with automated instrumentation. The lid mechanism has a compact design enabling it to function in very small spaces, and therefore on very compact instrumentation. It is also designed to be conveniently operable by software programming and with a minimum of maintenance or operator intervention. Also provided is an automated laboratory instrument having a lid mechanism of the invention.

In a first aspect the present invention provides a lid mechanism for securing a sample container. In this aspect the lid mechanism comprises several components, including a nut positioned around a jackscrew; a motor translationally attached to the nut for driving rotational motion of the nut around the jackscrew and vertical motion of the jackscrew; a main shaft positioned around the jackscrew with a bearing support positioned on the main shaft; a moving support comprising a bearing guide track and positioned on the main shaft so that the bearing support is positioned within the bearing guide track; and a lid plate positioned on the moving support so that vertical movement of the moving support causes vertical movement of the lid plate and rotational movement of the moving support causes rotational movement of the lid plate.

In one embodiment the jackscrew is connected to the moving support in a relation so that vertical movement of the jackscrew causes vertical movement of the moving support. The bearing guide track can be substantially arc shaped and can have a substantially vertical portion and a substantially diagonal and/or substantially horizontal portion. Friction between the bearing support and an edge of the bearing guide track on the moving support can cause rotational movement of the moving support. Displacement of the bearing support within the substantially vertical portion causes the moving support to move in a substantially vertical direction, and displacement of the bearing support within the substantially diagonal and/or substantially horizontal portion causes the moving support to move rotationally.

In one embodiment rotational movement of the moving support causes a lateral movement of the lid plate positioned on the moving support and the lateral range of motion can be about 80-100 degrees or about 90 degrees. In one embodiment the components are arranged so that the motor is translationally attached to a pulley that drives the rotational motion of the nut around the jackscrew and vertical motion of the jackscrew.

In another aspect the invention provides an automated laboratory instrument comprising a lid mechanism described herein. The automated laboratory instrument has a sample container containing one or more sample wells and the lid mechanism covers or exposes samples in the sample container. Lateral movement of the lid plate exposes at least one sample well in the sample container. In some embodiments the automated laboratory instrument is a temperature controlled chamber or a thermocycler. In some embodiments of the automated laboratory instrument movement of the moving support in the vertical direction occurs to an extent that the lid plate is lifted vertically clear of the sample container. And lateral movement of the lid occurs in an amount sufficient to expose at least a portion of the sample container and allow access to one or more samples in the container.

These and other objects and features of the invention will become more fully apparent when the following detailed description of the invention is read in conjunction with the accompanying drawings.

DETAILED DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 2A-2C provide an illustration of one embodiment of the lid mechanism of the present invention.

DETAILED DESCRIPTION OF THE INVENTION

The present invention provides a lid mechanism for laboratory instrumentation, such as an automated laboratory instrument. The mechanism is sized and operates in a manner that is suitable for compact laboratory instrumentation. By utilizing a clever design the lid mechanism of the invention provides a lid that can be operated in an automated fashion in small spaces, particularly vertically limited spaces, and further allows additional automated instrumentation to access samples present within a sample container because the lid can be rotated completely out of the way. In some embodiments the lid mechanism of the invention accomplishes this using only a single motor.

Figure 1:
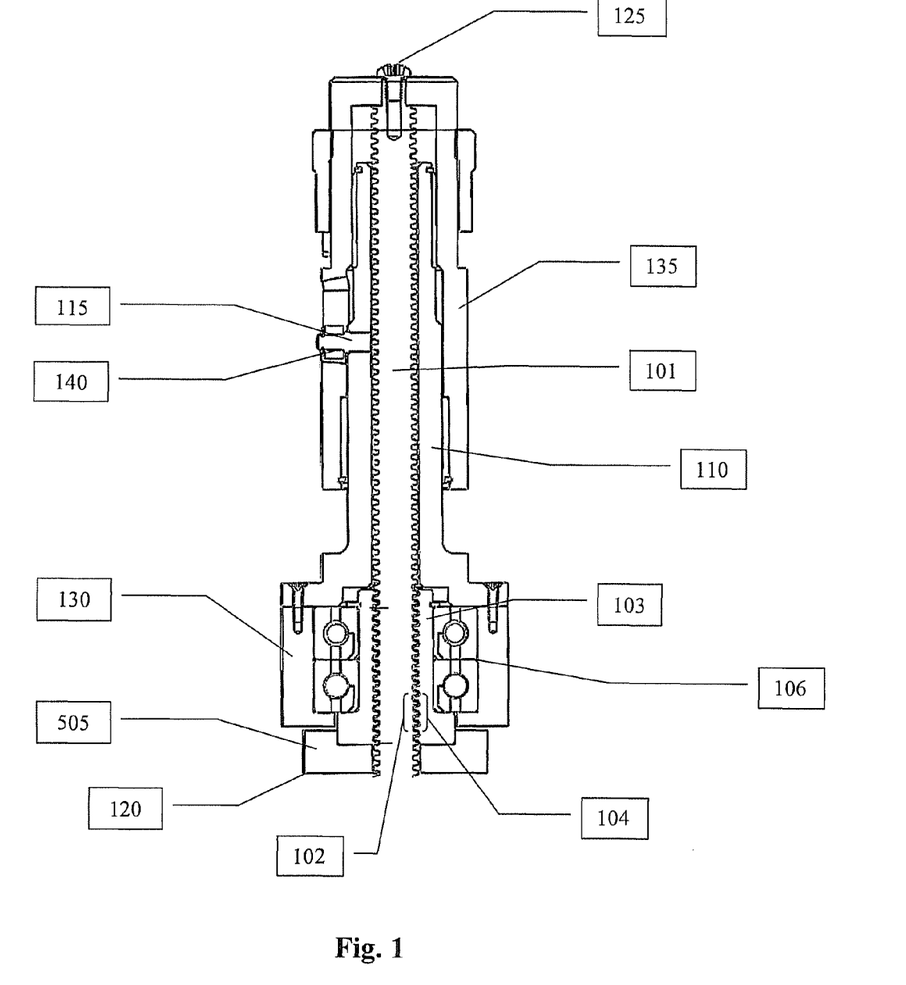
FIG. 1 provides a cross-sectional view of one embodiment of a lid mechanism of the present invention.

With reference to FIG. 1 there is depicted an embodiment of a lid mechanism of the invention, a jackscrew 101 is present near the center of this aspect of the mechanism and a nut 103 positioned around the jackscrew. The lid mechanism contains a motor 501 for driving rotational motion of the nut around the jackscrew. In the embodiment depicted (in FIG. 5) the motor is translationally attached to the nut 103. The jackscrew 101 has a threaded portion 102, which is threaded at a specific pitch. There is also a nut 103 positioned on or around or partially around the jackscrew. The nut can be positioned at least partially around the circumference of the jackscrew. The nut contains a threaded portion 104 that is mated to a threaded portion 102 of the jackscrew so that rotation of the nut around the jackscrew causes the jackscrew 101 to move vertically upwards or downwards. Thus, in this embodiment the jackscrew does not move rotationally but moves vertically in an up and down motion, which motion is driven by rotation of the nut around the jackscrew. The nut 103 is held substantially in place by radial bearings 106, which can be covered by a bearing cap 130. There is also a main shaft 110 that is positioned on or around or partially around the jackscrew (e.g. at least partially around the circumference of the jackscrew) and has a bearing support 115 positioned thereon. In one embodiment the main shaft 110 is a generally tubular shaped structure that surrounds the jackscrew. The main shaft can completely surround the circumference of the jackscrew. The main shaft can be fastened or attached to the jackscrew so that it moves vertically with the jackscrew and/or so that it does not move independently of the jackscrew.

The lid mechanism further contains a moving support 135, which can be attached to the jackscrew 101, for example by a screw 125 or other fastener. In the embodiment depicted there is present a lid plate 201 (FIG. 2) fastened or attached to the moving support and that moves with the moving support. Thus, in this embodiment vertical movement of the moving support causes vertical movement of the lid plate, and rotational movement of the moving support causes rotational movement of the lid plate. The moving support 135 has a bearing guide track 140 as a part of the component or associated with it. The bearing guide track 140 can take the form of a channel within the body of the moving support. In the embodiment depicted the moving support 135 is positioned on or around the main shaft 110 and/or the jackscrew so that the bearing support 115 is positioned within the bearing guide track 140 and the bearing guide track moves around the bearing support 115. The screw 125 fastens the moving support 135 to the jackscrew 101 and the moving support 135 is free to rotate laterally about the jackscrew 101 as depicted in FIGS. 2A-C.

Figure 4:
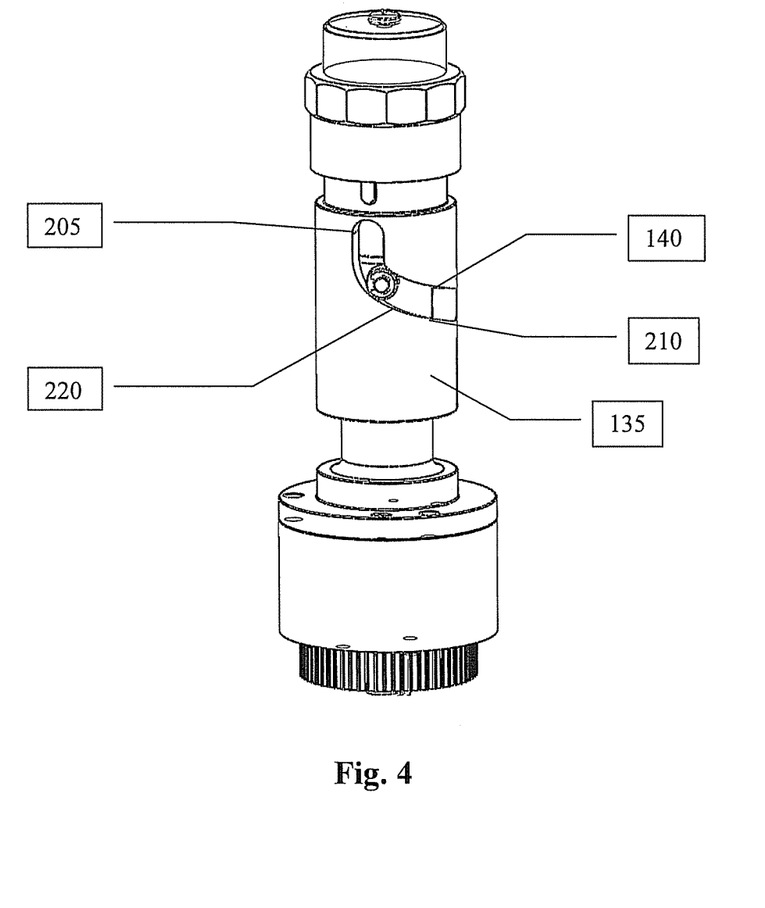
FIG. 4 shows a close up of an embodiment of the moving assembly and bearing guide track of the lid mechanism.

In one embodiment the bearing guide track 140 is substantially arc shaped and has a substantially vertical portion (FIG. 4, 205) and a substantially diagonal 220 or horizontal portion 210. When the jackscrew is moved in an up and down direction it thus causes corresponding movement of the moving support. In the embodiment depicted friction between the bearing support 115 and an edge of the bearing guide track 140 on the moving support causes rotational movement of the moving support as the moving support is forced to rotate around the bearing support. By substantially vertical is meant at an angle of from about 75 to about 105 degrees (or from 80 to about 100 degrees or about 90 degrees) relative to level. By substantially diagonal is meant at an angle of from about 25 to about 74 degrees (or from about 35 to about 55 degrees or about 45 degrees) relative to level. By substantially horizontal is meant from 0 degrees to about 24 degrees (or from 0 degrees to about 10 degrees or about 0 degrees) relative to level.

The lid mechanism has a nut 103 that rotates around the jackscrew 101. In the embodiment depicted the nut 103 has a bearing cap 130 and radial bearings 106 that secure the nut in position. The nut 103 also has a threaded interior surface 104 so that rotation of the nut around the jackscrew causes the jackscrew to move laterally in an up and down direction. When the jackscrew 101 is moved in a vertical up and down direction by rotation of the nut 103, the moving support 135 moves or is carried with it correspondingly. Because the bearing support 115 of the main shaft 110 is positioned within the bearing guide track 140 of the moving support 135 when the jackscrew 101 moves in a vertical direction and the moving support 135 moves or is carried with it, the moving support 135 is forced to rotate around the jackscrew 101 and main shaft 110. The lid plate 201, which is attached to the moving support is therefore also forced to also rotate laterally.

Figure 2A:
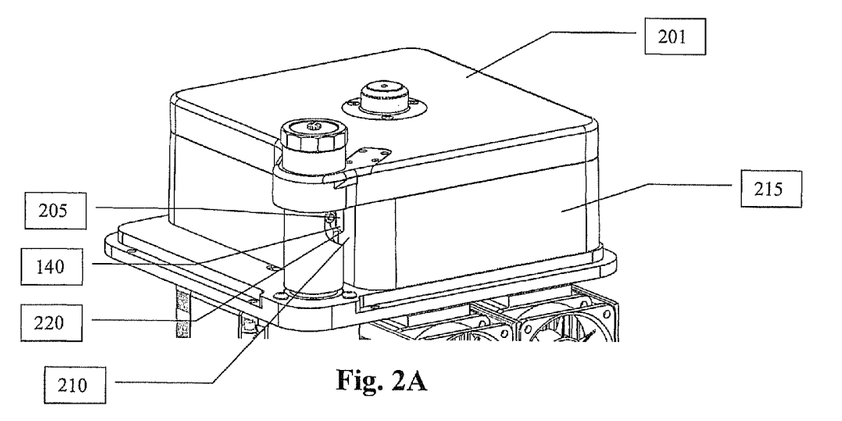
FIG. 2A shows the lid mechanism in the closed position.
Figure 2B:
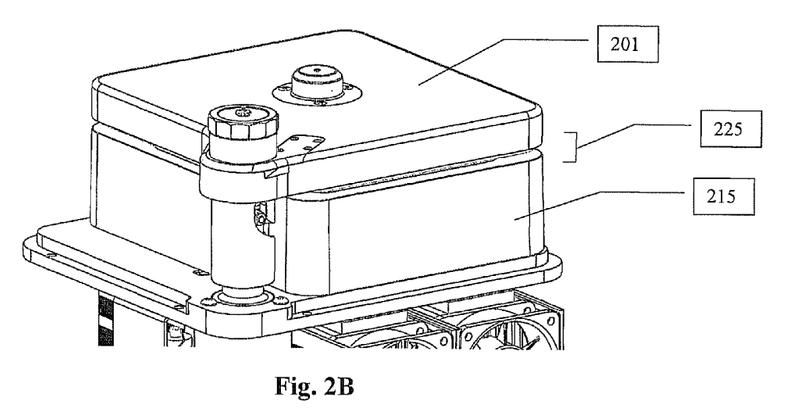
FIG. 2B shows the partially open position.
Figure 2C:
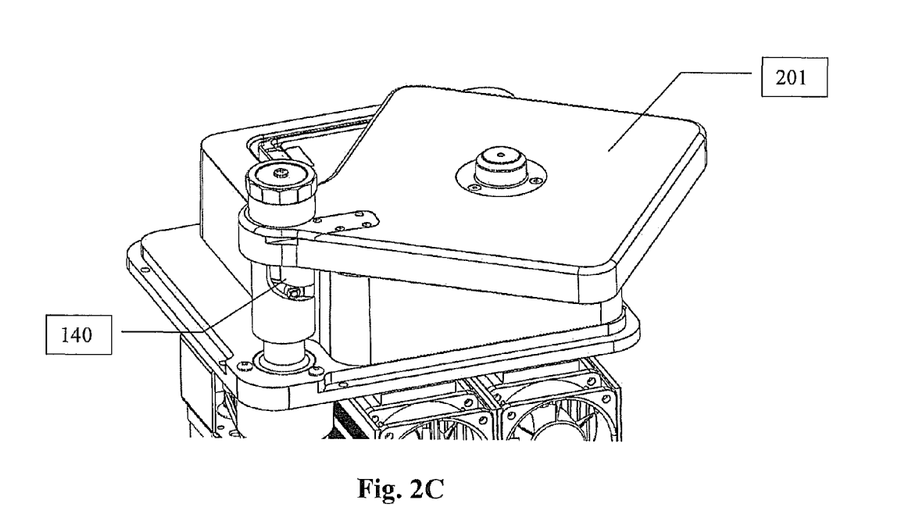
FIG. 2C shows the open position with the lid plate moving laterally to provide access to sample wells.

As depicted in FIG. 2A-C, the relationship of the components is such that displacement of the bearing support 115 within the substantially vertical portion of the bearing guide track causes the moving support 135 to move in a substantially vertical ("up and down") direction, and displacement of the bearing support within the diagonal and/or horizontal portion causes the moving support to move at least partially rotationally, and can also cause it to move vertically. The lid plate 201 is attached to the moving support 135, so that rotational or lateral movement of the moving support causes a corresponding rotational or lateral movement of the lid plate positioned on the moving support. The lateral range of motion can be from 0 to 360 degrees, but in various preferred embodiments is from 30° to 150°, or from 60° to 120° or from 80° to 100° or about 90 degrees.

In one embodiment the motor 501 is translationally attached to a belt 505, which in turn is translationally attached to a pulley 120 and drives rotation of the nut around the jackscrew (which forces the jackscrew to move vertically) through the pulley but the person of ordinary skill will realize that other translational mechanisms can also be used. The motor is not shown in FIG. 1 but can be positioned in any convenient location so it can drive the pulley. In the embodiment depicted the pulley 120 receives its rotational power from the motor causing movement of the pulley and consequent movement of the nut 103. Rotational movement of the nut causes the jackscrew to move vertically.

The lid mechanism of the invention is suited for various laboratory or industrial applications, or for use in a robot. In one embodiment the lid mechanism is suitable to provide a lid over a sample plate or sample container. Thus in one embodiment the lid mechanism of the present invention is comprised on or functionally incorporated within an automated laboratory instrument or a robot. The automated laboratory instrument can have a sample container containing one or more sample wells and the lid mechanism can cover the samples or sample wells when in the closed position or expose the samples or sample wells when in the open position. As the lid mechanism moves to the open position the lateral movement of the lid plate exposes and provides access to at least one sample well in the sample container. A sample container can be any container that carries or holds samples. In one embodiment the sample container has a box or tray that contains samples, e.g. samples in test tubes or centrifuge tubes. The samples can be contained within sample wells, such as a structure that contains the lower part of a sample tube. The lid of the sample container can be a lid mechanism of the invention.

In one embodiment the automated laboratory instrument is a thermocycler or temperature controlled chamber, but it can also be any laboratory instrument where there would be a benefit from application of the invention, more examples being a chiller or incubator. In one embodiment movement of the moving support in the vertical direction occurs to an extent enabling the lid plate is lifted vertically clear of the sample container to an extent allowing a lateral movement of the lid plate without being blocked by the lip of the sample chamber. Lateral movement occurs to an extent sufficient to expose at least a portion of the sample container and allow access to one or more samples in the container. In a particular embodiment the lateral movement exposes or enables access to all samples in the sample container.

Figure 3:
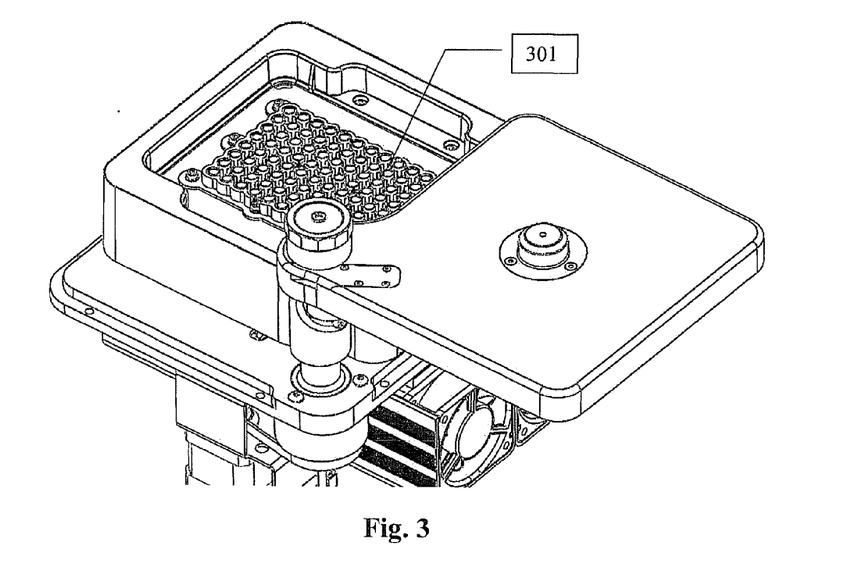
FIG. 3 shows an embodiment of the lid mechanism in the fully open position.

With reference to FIG. 2 there is depicted a lid mechanism of the invention incorporated into an automated laboratory instrument, which in this embodiment is a thermocycler. In FIG. 2a the lid mechanism is in the closed position and the lid plate 201 closes the sample chamber 215. In various embodiments the sample chamber 215 can be the container (e.g. a tray) that holds the samples or a chamber that holds the sample container or samples. In the closed position the lid plate shields the samples in the sample chamber from light and can allow no light to enter the sample chamber. There is also indicated on the moving support 135 the bearing guide track 140, which has a substantially vertical portion (205) and a substantially diagonal portion (220) and/or a substantially horizontal portion (210). In FIG. 2b is depicted the lid plate 201 in an open, raised position. A clearance 225 is visible and the lid plate is clear of the sample chamber 215. In this position the jackscrew 101 has been moved vertically to a lower position causing the bearing support 115 to be pulled down in the bearing guide track 140 and thus causing the moving support 135 to also be lowered. Due to friction of the bearing support with the side of the bearing guide track the moving support 135 is forced to rotate laterally into an open position (FIG. 2c). The lid plate rotates in an amount sufficient to expose at least a portion of the sample container and at least one sample 301 within the sample container, and thus allow access to one or more samples 301 in the sample chamber. FIG. 3 depicts the lid mechanism in the fully open position providing access to samples 301 in the sample chamber, and the lateral movement of the lid plate is approximately 90 degrees.

As the bearing support approaches the substantially horizontal portion of the bearing guide track (and maximum rotational motion) friction is increased between the bearing support and the side of the bearing guide track. Therefore, the lid mechanism will function most efficiently in some embodiments when the substantially horizontal portion of the bearing guide track is not truly horizontal, at least for no more than a minimal space of motion. By properly designing the shape of the bearing guide track a smooth vertical and horizontal rotation of the lid plate is achieved.

Figure 5:
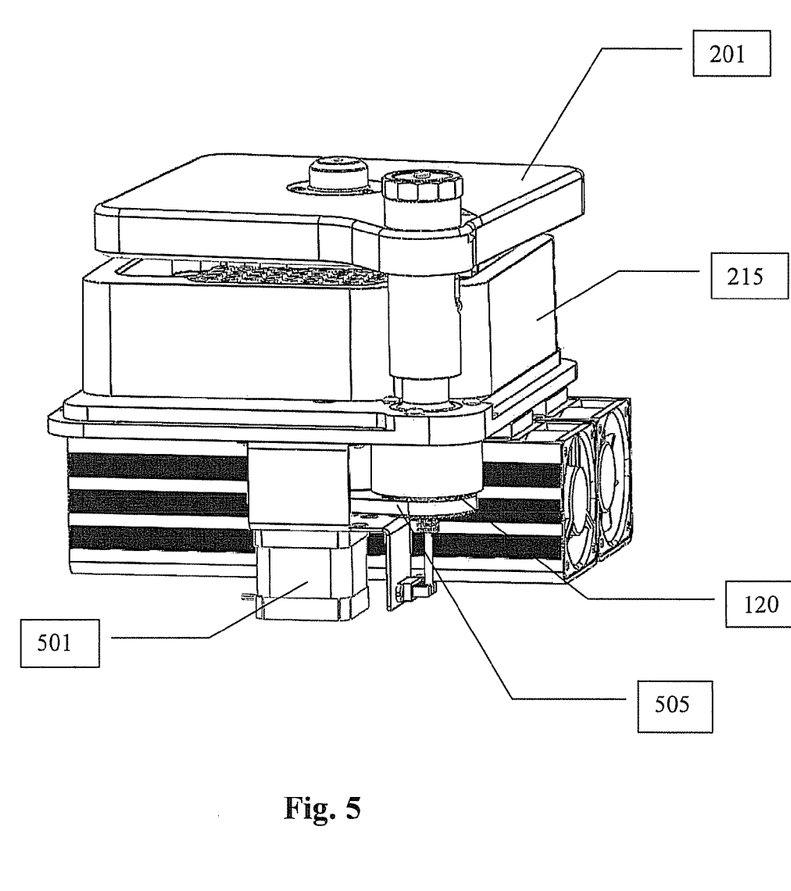
FIG. 5 is a schematic illustration of a lid mechanism of the invention.

FIG. 5 represents an embodiment of the lid mechanism of the invention on an automated laboratory instrument. In this embodiment rotational movement is translated to the lid plate via a motor 501 connected to a belt 505, and two pulleys 120 (one shown). Persons of ordinary skill in the art with reference to this disclosure will realize other methods of translating a force of movement from a power source to the mechanism. For example, a direct-drive motor can be connected to the jackscrew and provide rotational force. In another embodiment the belt and motor can be replaced with another power source or an internal nut motor, which can eliminate the need for one or more of the pulleys and bearings. An example of such a power source is a linear actuator, which are known in the art. In one embodiment the power source can be mounted on the bottom portion of the main shaft and the jackscrew extends into or through the power source. In various additional embodiments vertical motion can be translated to the moving support through a hydraulic actuator, a pneumatic actuator, a piezoelectric actuator, an ultrasonic motor, an electro-mechanical actuator, a linear motor, a telescoping linear actuator such as a helical band actuator, a rigid belt actuator, a rigid chain actuator, a segmented spindle, or a cam drive. In addition to these embodiments the person of ordinary skill with resort to the present disclosure will realize additional methods of providing power to move the components of the lid mechanism.

The nut, jackscrew, and other components of the lid mechanism can be made of any suitable material. In different embodiments the components can be made of, for example, a plastic, steel, or a suitable metal. Persons of ordinary skill with resort to the present disclosure will also realize other suitable materials that can be employed in manufacturing the components described herein.

The lid mechanism of the invention performs its functions in situations where the vertical clearance above the lid plate of the mechanism is limited. The vertical space above the lid plate can be a space of less than 6 inches, or less than 5 inches or less than 4 inches or less than 3 inches or less than 2 inches or less than 1 inch. The vertical space is measured by the distance above the lid plate in the closed position that the lid plate can rise before encountering an obstruction.

In one embodiment the jackscrew of the invention has a threaded portion, which is mated with a similarly threaded portion of an interior surface of the nut. The threaded portion of the jackscrew and/or interior surface of the nut can be a groove that rises along the exterior surface of the jackscrew at a particular pitch, which can be a defined pitch. A defined pitch is when the groove on the jackscrew rises (or falls) along the jackscrew by the same amount with each path traced around the circumference of the jackscrew. The nut can be of a complete circular shape or an incomplete circular shape with the interior surface threaded and of sufficient surface area so that it mates with the exterior surface of the jackscrew and drives movement of the jackscrew.

In one embodiment the bearing support and the main shaft can be formed as a single unitary component or as separate components that are fastened together or connected. FIG. 1 depicts a cross-section of the jackscrew and main shaft and the jackscrew can be positioned inside the main shaft and can be partially or completely surrounded by it. Thus, in some embodiments the main shaft can have one or more windows or openings in the component. The main shaft can have a bearing support either fastened to it or connected to it or otherwise present on it so that the main shaft and bearing support move together as a unit. In one embodiment the lid plate is attached to, fastened to, or otherwise connected to the moving support. The bearing support can have a variety of shapes, such as a small knob or button.

Some components of the lid mechanism are translationally attached to other components. When components are translationally attached, they are linked so that one or more components provide rotational or kinetic energy to one or more other components. Thus, in one embodiment one or more motors of the lid mechanism can be translationally attached to one or more pulleys. This means that kinetic energy (which can be rotational energy) generated by the motor is translated to a belt and/or pulley, and these components translate that energy to a rotational force of the nut, which then powers vertical movement of the jackscrew. This translational attachment can be direct, but can also be indirect. When the translational attachment is indirect there are additional components in between the component generating the energy and the component to which the energy is transmitted or translated.

Some embodiments of the invention also utilize a belt and pulley system. A belt and pulley system is characterized by two or more pulleys in contact with a common belt and connected thereby, which allows for mechanical power, torque, or kinetic energy to be transmitted from a power source across axles. One or more of the pulleys can be driven by the power source and the power translated to another axle by a connected belt. In the invention the pulleys can be of differing diameters to achieve a mechanical advantage. In the invention the belt can also be substituted with a chain, gear train, or other component that is capable of transmitting energy from one axle to another. An axle is a central shaft that exhibits rotational motion that can be transmitted to a pulley. A pulley is a wheel or generally circular component positioned on an axle or central shaft. The wheel or pulley is desirably circular in shape but is not necessarily so. As an example in one embodiment a pulley connected to the motor and a pulley connected to the nut can be considered "axles" and are connected by a belt which transmits rotational motion from the motor to the nut.

The lid mechanism of the invention can be present as part of a laboratory instrument, which in one embodiment is an automated laboratory instrument. In a particular embodiment the automated laboratory instrument that contains the lid mechanism can be a thermocycler (or thermal cycler) or temperature controlled chamber, on which PCR or other DNA manipulation or amplification techniques are performed in an automated fashion. "Automated" can mean fully automated, i.e. requiring no human participation after a reaction is net up and begun, or can be partially automated, i.e. a human must intervene to perform one or two or more than two steps for the reaction to proceed after the reaction is begun. But the laboratory instrument can be any laboratory instrument where it is desirable to protect samples in a sample chamber.

The discussion of the general methods given herein is intended for illustrative purposes only. A number of embodiments of the invention have been described. Nevertheless, it will be understood that elements of the embodiments described herein can be combined to make additional embodiments and various modifications may be made without departing from the spirit and scope of the invention. Accordingly, other embodiments, alternatives and equivalents are within the scope of the invention as described and claimed herein and will be apparent to those of ordinary skill in the art upon review of this disclosure. Headings within the application are solely for the convenience of the reader, and do not limit in any way the scope of the invention or its embodiments.

The invention claimed is:

1. A lid mechanism for securing a sample container, comprising:
   a nut positioned around a jackscrew;
   a motor translationally attached to the nut for driving rotational motion of the nut around the jackscrew and vertical motion of the jackscrew;
   a main shaft positioned around the jackscrew with a bearing support positioned on the main shaft;
   a moving support comprising a bearing guide track and positioned on the main shaft so that the bearing support is positioned within the bearing guide track;
   a lid plate positioned on the moving support so that vertical movement of the moving support causes vertical movement of the lid plate and rotational movement of the moving support causes rotational movement of the lid plate.

2. The lid mechanism of claim 1 wherein the jackscrew is connected to the moving support in a relation so that vertical movement of the jackscrew causes vertical movement of the moving support.

3. The lid mechanism of claim 1 wherein the bearing guide track is substantially arc shaped and has a substantially vertical position and a substantially diagonal and substantially horizontal position.

4. The lid mechanism of claim 3 wherein friction between the bearing support and an edge of the bearing guide track on the moving support causes rotational movement of the moving support.

5. The lid mechanism of claim 4 wherein displacement of the bearing support within the substantially vertical portion causes the moving support to move in a substantially vertical direction, and displacement of the bearing support within the substantially diagonal and/or substantially horizontal portion causes the moving support to move rotationally.

6. The lid mechanism of claim 5 wherein the rotational movement of the moving support causes a lateral movement of the lid plate positioned on the moving support.

7. The lid mechanism of claim 6 wherein the lateral range of motion is about 80-100 degrees.

8. The lid mechanism of claim 7 wherein the lateral range of motion is about 90 degrees.

9. The lid mechanism of claim 1 wherein the motor is translationally attached to a pulley that drives the rotational motion of the nut around the jackscrew and vertical motion of the jackscrew.

10. An automated laboratory instrument comprising a sample container containing one or more sample wells and the lid mechanism of claim 1 covers or exposes samples in the sample container.

11. The automated laboratory instrument of claim 10 wherein lateral movement of the lid plate exposes at least one sample well in the sample container.

12. The automated laboratory instrument of claim 10 wherein the sample container is enclosed in a temperature controlled chamber.

13. The automated laboratory instrument of claim 11 wherein movement of the moving support in the vertical direction occurs to an extent that the lid plate is lifted vertically clear of the sample container.

14. The automated laboratory instrument of claim 11 wherein the lateral movement of the lid occurs in an amount sufficient to expose at least a portion of the sample container and allow access to one or more sample wells in the sample container.

* * * * *